United States Patent [19]

Bellingham et al.

[11] Patent Number: 5,109,874
[45] Date of Patent: May 5, 1992

[54] WOUND PATCH

[75] Inventors: Godfrey Bellingham, Lake Elmo; Julia A. Lord, Eagan, both of Minn.

[73] Assignee: Bellingham Medical Inc., Lake Elmo, Minn.

[21] Appl. No.: 732,172

[22] Filed: Jul. 18, 1991

[51] Int. Cl.⁵ .............................................. A61F 13/00
[52] U.S. Cl. ...................................... 128/888; 128/155
[58] Field of Search ............... 128/888, 155, 156, 157, 128/893, 894; 152/367, 371

[56] References Cited

U.S. PATENT DOCUMENTS

| | | | |
|---|---|---|---|
| 3,529,416 | 9/1970 | Chamberlain | 128/888 |
| 3,782,378 | 1/1974 | Page | 128/888 |
| 4,341,209 | 7/1982 | Schaar | 128/156 |
| 4,399,816 | 8/1983 | Spangler | 128/888 |
| 4,484,574 | 11/1984 | DeRusha | 128/856 |
| 4,499,896 | 2/1985 | Heinecke | 128/155 |
| 4,641,641 | 2/1987 | Strock | 128/888 |
| 4,733,659 | 9/1987 | Edenbaum | 128/156 |
| 4,738,257 | 4/1988 | Meyer | 128/156 |
| 4,758,231 | 6/1988 | Lang | 128/155 |
| 4,773,409 | 9/1988 | Cliento | 128/156 |
| 4,786,282 | 11/1988 | Wagle | 128/156 |
| 4,832,009 | 5/1989 | Dillion | 128/156 |
| 4,867,150 | 9/1989 | Gilbert | 128/856 |
| 4,917,112 | 4/1990 | Kalt | 128/155 |
| 5,056,510 | 10/1991 | Gilman | 128/155 |
| 5,060,642 | 10/1991 | Gilman | 128/888 |

Primary Examiner—Robert A. Hafer
Assistant Examiner—Michael Brown
Attorney, Agent, or Firm—Jacobson & Johnson

[57] ABSTRACT

A dynamic wound patch having a gas and liquid impermeable member that is adhesively sealed to the skin around a wound to temporarily form a barrier over the wound to prevent the ingress or egress of gases and liquids through the wound patch to permit a user to engage in physical activity without concern for contaminants entering or leaving the wound area and a method of insitu making a non-stick island on a wound patch.

9 Claims, 2 Drawing Sheets

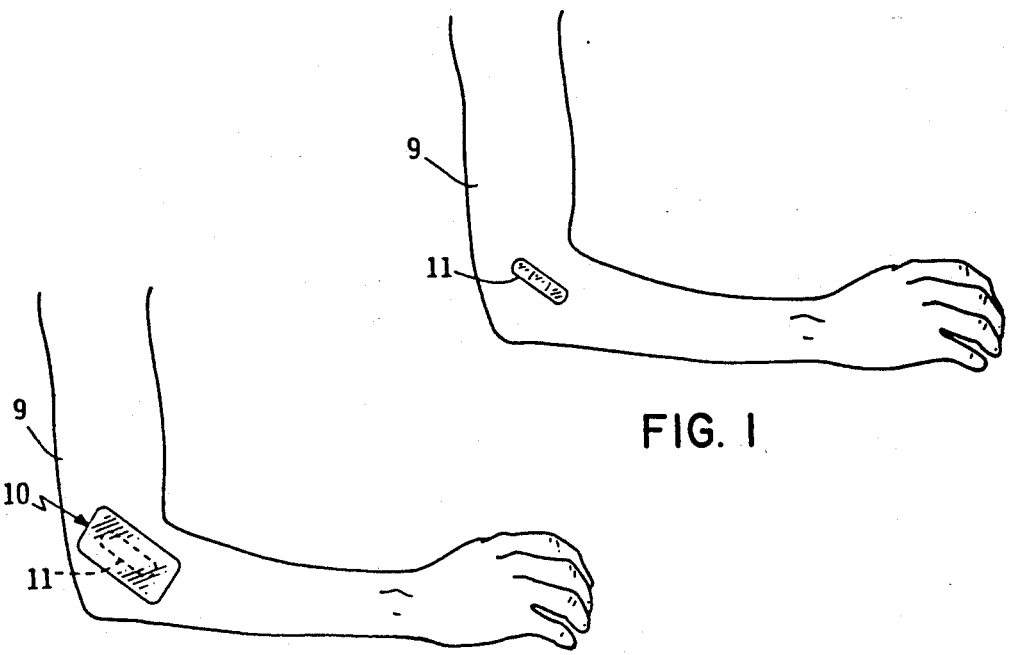
FIG. 1
FIG. 2
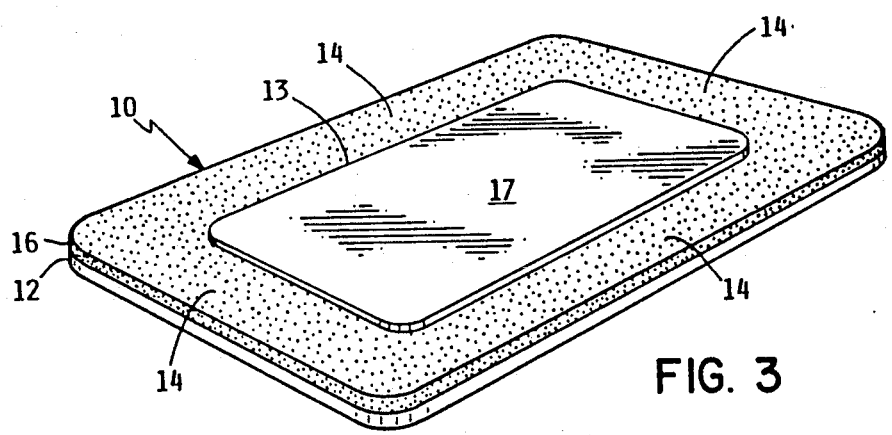
FIG. 3
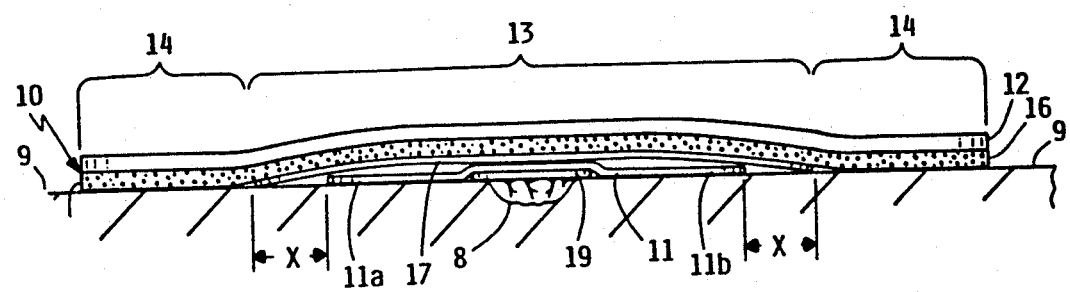
FIG. 4

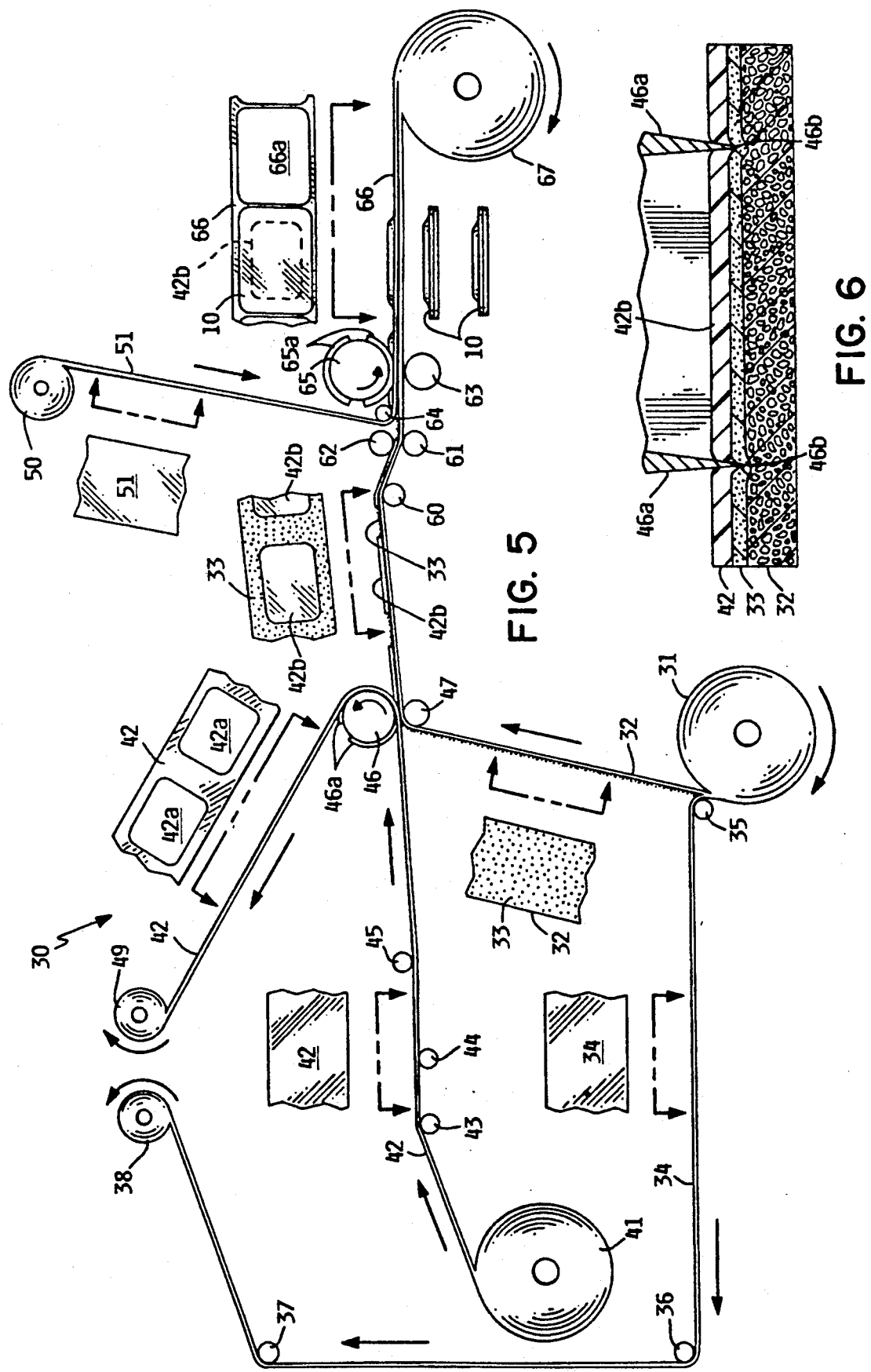

WOUND PATCH

FIELD OF THE INVENTION

This invention relates generally to short term protective wound coverings and more specifically to a dynamic liquid and gas impermeable wound patch to prevent ingress and egress of contaminates through the wound patch for a period of a few hours while a user engages in a physical activity and a method of making a nonbreathable and liquid impermeable wound patch.

BACKGROUND OF THE INVENTION

The concept of protective coverings or bandages for a wound to promote healing of a wound is well known in the art. Typically, most open skin wounds require both protection from the environment and exposure to the atmosphere. It has been generally found that a porous wound covering that breaths or lets air into the wound either through the bandage covering the wound or through openings along the side of the bandage is useful to facilitate the healing process. In order to keep contaminants such as moisture and dirt out of the wound and still promote healing of the wound the bandage is breathable and is made from a gas permeable and water impermeable material.

The use of water impermeable materials in prior art bandages allows the user to shower or bathe without having the bandage fall off, however, such bandages do not prevent contaminates from contacting the wound while the user showers or bathes.

Still other prior art bandages may be made of materials that are gas impermeable or liquid impermeable, however, such bandages are constructed to only partially shield a wound since they typically have side openings to allow air to enter the wound. Thus while the bandages material is gas impermeable or liquid impermeable the bandage when placed on the wound permits the wound to breath.

In addition there is another class of bandages that are occlusive and have some type of gel or liquid absorbing material such as hydrocolloids. Typically these occlusive bandage are used on hospital or nursing home patients that have pressure sores or dermal ulcers from continual confinement in a bed. Under such conditions it is best to keep the wound moist to promote healing. One such bandage is shown in the U.S. Pat. No. 4,738,257. The occlusive wound dressing uses a water absorbable material that maintains the wound under moist conditions by preventing outward migration of the wound exudate. A tackifier polymer is used to adhere the wound dressing directly to the wound and the skin. Even in this application it is preferred to have the backing material porous or air permeable to allow excretions to evaporate into the air thus prolonging the liquid absorbing capacity of the dressing.

Unfortunately, in certain situations the prior art bandages provide inadequate protection for the user to safely engage in a physical activity. For example, if a user wants to participate in a physical activity for a few hours in the direct presence of contaminates in a typical room temperature environment of 50 to 80 degrees Fahrenheit the prior art bandages provide inadequate protection since they also allow contaminates to enter the wound site through the air passages created by vent holes in the bandage backing and imperfect sealing around the periphery of the bandages. If contaminates enter the wound area it can cause infection in the open wound and thus prolong the healing period. Consequently, such prior art bandages while providing limited wound protection do not allow a person to engage in physical activities in the direct presence of contaminants without increasing the risk of infection. For example, if a user needs to come in direct contact with chemically treated water containing alcohols or cleaning agents that are being vaporized into the atmosphere the person needs to protect or isolate the wound from direct contact with either the water or the harmful vapors. Conversely, if the user needs to temporarily work in an environment where the liquid and gas excretions from the wound may be harmful to another person the user needs to isolate and temporarily prevent the liquid and gas excretions of the wound from escaping from the bandage area. In both situations it would be desirable if one could isolate the contaminates on one side of the dressing, however, the care and treatment of wounds usually requires that the bandages allow air to contact the wound to expedite the healing.

Typically, the prior art solution for contamination of a bandage and a wound during a physical activity is to replace the bandage with a fresh bandage after the user completes the physical activity in the harmful environment. However, replacing the bandage does not prevent contaminates from entering the wound during the physical activity.

The present invention in contrast to the prior art bandages is not considered a bandage that one would place on a wound to provide long term protection of the wound during the healing process. In contradistinction the present invention is a temporary wound patch that provides a dynamic wound and bandage covering that flexes with the skin movement and does not stick to the underlying protective bandage or wound. The patch is made from a nonbreathable material that can be applied over the wound for a period of a few hours to totally isolate the wound from the environment while the person engages in a physical activity. That is, the present invention permits a user to provide a room temperature wound patch that temporarily encapsulates and seals around the wound or around a bandage located over the wound with a protective patch that is both air and liquid impermeable to isolate the wound and prevent the wound from being contaminated during the physical activity of the user. The patch is made of a material that flexes and dynamically conforms to the movement of the body. The central region of the patch contains a non-stick region that allows the patch to move without pulling on or disturbing the wound. After the user completes the physical activity the user removes the wound patch. Thus the present invention allows a wound to be protected by a patch that is both gas and liquid impermeable for up to a few hours. Since the patch only covers the wound for a short period of time and the patch has a non-stick island it does not adversely affect the healing process and thus eliminates the setbacks in healing caused by having contaminants infect the wound.

DESCRIPTION OF THE PRIOR ART

U.S. Pat. No. 4,341,209 shows a pressure sensitive adhesive bandage with a closed cell backing sheet that fits only partially around a wound.

U.S. Pat. No. 4,773,409 shows an occlusive wound dressing that contains a water swellable or water absorbing agent where the adhesive contacts the wound site and the surrounding skin. The dressing is placed over the wound to absorb the wound exudate.

U.S. Pat. No. 4,738,257 shows another occlusive wound dressing that uses a water absorbable material that maintains the wound under moist condition by preventing outward migration of the wound exudate.

U.S. Pat. No. 4,733,659 shows a foam bandage that has an outer layer that has a moisture vapor permeable, moisture impermeable skin to provide a water and bacteria proof protective outer layer. Although the outer skin is made from a water and bacterial proof protective outer layer the sides of the bandage are left open and permit water and bacteria to enter.

U.S. Pat. No. 4,832,009 shows a bandage with a vapor permeable and water impermeable backing to place over a wound during the healing process. While this bandage has a water impermeable backing and is sealed around the wound it specifically requires the bandage to be air permeable or breathable to promote healing.

U.S. Pat. No. 4,867,150 shows a wound dressing with an improved dressing that can be left in contact with the wound longer then normal.

U.S. Pat. No. 4,484,574 shows a pressure sensitive tape with a closed-cell polymer backing strip that is used to hold down a bandage or as an athletic wrap.

BRIEF SUMMARY OF THE INVENTION

Briefly, the present invention comprises a dynamic, elastic, non breathable wound patch that is adhesively sealed to the skin around the periphery of a wound to temporarily form a barrier over the wound to prevent the ingress or egress of gases and liquids through the wound patch to allow a user to engage in physical activity in direct contact with contaminants without concern for contaminants entering or leaving the wound area. The process of the invention permits one to reuse the product liner and to insitu form the nonstick islands on the wound patches.

BRIEF DESCRIPTION OF THE DRAWINGS

FIG. 1 shows an arm with the prior art bandage located on a broken skin wound;

FIG. 2 shows my invention of a wound patch located over both the prior art bandage and the broken skin wound on a user's arm;

FIG. 3 shows a pictorial view of the underside of my invention of a wound patch;

FIG. 4 shows a cross-sectional view of my invention covering a bandage and wound on a persons arm;

FIG. 5 shows a schematic of a system for making the wound patches; and

FIG. 6 shows an enlarged view of the insitu forming of a nonstick directly on the adhesive backing of the nonbreathable and liquid impermeable material of the wound patch.

DESCRIPTION OF THE PREFERRED EMBODIMENT

In order to understand how the present invention can be used to temporarily prevent ingress of gases or liquids with an existing protective bandage reference should be made to FIG. 1 and FIG. 2. FIG. 1 reference numeral 11 identifies a typical strip type bandage located over a broken skin wound on the arm of a the user. Typically, bandage 11 may have a water impermeable backing and a pad located on a portion of the backing to absorb excretions from the wound and to protect the wound during the healing process. Strips of adhesive are located on each end of the bandage to hold bandage 11 in place over the wound.

FIG. 2 is an identical view of FIG. 1 except may flexible, elastic, wound patch 10 is located on top of bandage 11 and adhesively secured to the skin around the outer peripheral region of skin located around bandage 11. That is, in order to provide a temporary dynamic protection to both the wound and bandage 11 I encapsulate both the wound and bandage 11 with my wound patch 10. Wound patch 10 of the present invention is temporarily placed over both bandage 11 and the wound for a period of up to a few hours while the person engages in the activity. When the person has completed the activity wound patch 10 is removed to expose bandage 11 located on the wound.

The present invention should not be confused with bandages that are applied to wounds for extended periods of days or weeks to both protect and promote healing of the wound. While the present invention provides a short term contamination barrier for the wound it does so in an entirely different manner than the prior art bandages that provide long term wound protection. Typically, prior art bandages generally rely on some type of absorption pad or some type of breathable material to enhance the healing process. The present invention relies on neither and does not provide any material to enhance the healing process. In stead the present invention provides temporary protection from contaminates passing into or out of a wound. Thus the present invention prevents the healing process from being retarded or being set back due to infections caused by direct contact with typical environmental contaminates but it does not enhance the healing process as do prior art bandages. After use which may typically be a few hours the user must remove and discard the present invention since it is not a dressing for enhancing the healing of a wound.

FIG. 3 shows wound patch 10 comprises a flexible and resilient layer of material 12 that has sufficient flexibility to dynamically conform to the movement of the skin underlying the wound patch. The materiel 12 comprises a liquid impermeable and gas impermeable material that prevents ingress or egrss of gases or liquids through the flexible and resilient layer of material 12. Wound patch 10 has an interior region 13 and a peripheral region 14.

Located on the interior a region 13 is a nonabsorbent and non-stick materiel 17 forming non-stick island that will not adhere to either a bandage or to a wound to allow a user to place the nonabsorbent and non-stick island directly over wound or a bandage on a person. The non-stick island is nonabsorbent and does not provide a reservoir for absorbing excretions from a wound.

The peripheral region 14 of wound patch 10 contains a layer of liquid and gas impermeable adhesive 16 that extends completely around the interior region 13 to coact with the flexible and resilient layer of material 12 to dynamically secure flexible and resilient layer of material 12 to the skin of a user. Once secured material 12 temporarily forms a liquid and gas impermeable barrier over a wound so that the user can participate in physical activities in the presence of contaminates without contaminating the wound or having the wound excretions contaminate the environment outside the wound patch.

I have found that a closed cell 1/32 inch thick polyethylene foam tape that is coated on one side with a high tack non-sensitizing medical grade adhesive makes an excellent short term gas and liquid impermeable barrier since both the adhesive and the polyethylene foam tape provide substantial short term liquid and gas impermeability at room temperature environments. One such tape useable in making my wound covering is manufactured and sold by Technographids Fitchburg Coated Products, Inc. The tape is sold for use in mounting electrocardiograph pads or grounding pads to the skin on the human body. I have found the material provides an excellent short term gas and liquid impermeable covering for a wound. The material is further characterized by having sufficient conformability to dynamically flex and bend in response to the flexing and bending of the human body. I have also found that the adhesive and the tape can coact sufficiently so that both the layer of polyethylene foam and the adhesive can flex and bend without being pulled free of the skin during normal physical motions of the user's body. In addition the polyethylene foam has sufficient resiliency so as to return to its original position without releasing from the users skin.

EXAMPLE ONE

In order to test the wound patch in a typically household environment encountered by a user wound patches were placed on both the stomach and the knee of the user by smoothing the wound patches directly to the skin. The user then proceed to take a bath in a bathtub containing a bath soap. The bathtub brought the contaminants in the water into direct contact with the user's unprotected skin and the exterior surface of the wound patches covering portions of the users skin. The wound patches were monitored at intervals of 5 minutes, 10 minutes and 15 minutes. No water or gas penetration of the wound patches was observed as the wound patches remained smoothly contoured to the skin. After completion of the bath the wound patches were removed and discarded.

EXAMPLE TWO

In order to test the wound patch in a typical dynamic physical activity such as swimming in a pool containing chlorinating chemicals several rectangular shaped wound patches each approximately 2 inches by 4 inches were placed on various locations on the body of the user. Swimming was selected since it is an activity that could bring both liquid and gas contaminants into direct contact with a wound. Two wound patches were placed on the calf, two on the thighs, two on the stomach two on the back and two on the elbow portion of the arm. The person then swam in a chlorinated swimming pool which was at a temperature of 80 degrees Fahrenheit for a period of an hour. The person routinely encounter depths of approximately three feet. The wound patches were monitored every 15 minutes for an hour. No water penetration or gas penetration of the the wound patch was observed as the bandages remained smoothly contoured to the skin. After completion of the swimming the wound patches were removed and discarded.

In each of the examples the wound patch provided a short term wound protection from both liquids and gases that eliminated the chances of further contamination of the wound. By eliminating infection of the wound by preventing direct contamination of the wound by the wound patch one is assured that the healing process can continue with the minimum of interruption of the user's normal schedule. In the preferred use of the wound patches the wound patch use should be limited to six continuous hours or less.

In order to illustrate how the wound patch 10 appears when covering a wound and bandage reference should be made to FIG. 4. FIG. 4 shows a portion of a users arm 9 that has a wound 8 that is covered by a protective bandage 11 having a pad 19 located directly over wound 8. Located on the end of bandage 11 are adhesive regions 11a and 11b that hold the bandage 11 directly over the wound 8. Located in an encapsulating relationship to bandage 11 is my protective wound patch 10. Note the non-stick island 17 projects a distance x beyond the ends of the bandage to ensure that the adhesive on the wound patch does not contact bandage 11. The adhesive 16 in the outer peripheral region 14 secures wound patch 10 to the user's skin. The adhesive 16 in the central region 13 secures the non-stick island 17 to the adhesive. Typically, the non-stick island can be a thin nonabsorbent material such as polyethylene film that provides flexibility without bulkiness. That is wound patch 10 lacks any substantial bulkiness in the center region that may interfere with the dynamic adherence of the wound patch to the skin around the wound.

Although my wound patch is shown in conjunction with a bandage it is also possible to temporarily place wound patch over a wound since the non-stick island and the adhesive are both sterile and will not hinder the healing process.

Referring to FIG. 5 reference numeral 30 identifies a system for forming our wound patches in a continuous process that permits one to reuse the product liner from the roll of closed cell polyethylene foam tape 31 as the product liner on the individual wound patches 10. System 30 also permits the insitu cutting of film islands on the foam tape without destroying the gas impermeability and liquid impermeability characteristics of the foam tape.

Reference numeral 31 identifies a roll of adhesive covered liquid and gas impermeable foam tape 32 having a layer of adhesive 33 and a releasable liner 34 located on top of the layer of adhesive 33. In operation of our system releasable liner 34 is stripped from roll 31 and passes over rollers 35, 36 and 37 where it is wound and stored on roller 38 for future use. In order to understand the nature of the strips passing through the system a portion of a top view of the various strips during various steps in the process are shown adjacent to the strips.

In operation of the system product liner 34 is stripped from roll 31 while the adhesive layer 33 and the foam tape 32 move upward around support roller 47 and between die cutting roller 46 and support roller 47 where a strip of polyethylene film 42 is secured over the entire face of the adhesive layer 33. The polyethylene film 42 is unwound over rollers 43, 44 and 45 before it passes between die cutting roller 46 and support roller 47. The die cutting roller 46 contains die cutting members 46a that cut the polyethylene film into inlands while the polyethylene film 42 is being adhesively fastened on foam tape 32. That is, the support roller 47 and die cutting roller 46 simultaneously force the polyethylene film 42 into contact with adhesive 33 on foam layer 32 and cut polyethylene film non-stick islands 42b that remain centrally secured to adhesive layer 33. The scrap skeleton polyethylene film 42, which has openings 42a formed by the die cutting roller 46, passes upward around roller 46 and is wound on roll 49.

The polyethylene islands 42b which are secured to adhesive 33 on foam tape 32 pass around rollers 60, 61 and 62. After passing between rollers 61 and 62 a removable product liner 51 is unwound from roll 50 and passes under roller 64 where it is secured to adhesive 33 located in the region outside islands 42b on foam tape 32. The foam tape 32 with the islands 42b, and product liner 51 then passes between rollers 63 and 65 where a die cutter 65a completely cuts through foam tape 32 to cut individual wound patches 10 from strip of foam tape 32. A mechanism (not shown) delivers the individual wound patches to a packaging area while the outer skeleton 65 of foam tape 32 having openings 66a winds around roller 67.

One of the features of the above process is that the product liner on foam tape 31 is stripped from foam tape 32 and wound on roller 38 for later use. That is product liner 38 is rolled on roll 38 and then reused on the next roll of as the product liner 51 for wound patch 10.

Another feature of the invention is that the insitu cutting of the film islands eliminates the difficult task of cutting and applying individual non-stick islands to the foam tape.

Referring to FIG. 6 reference numeral 46a identifies the die cutter having a cutting edge 46b that cuts though polyethylene film 42 to cut island 42b while film 42 is supported in tension on foam tape 32. Note the polyethylene film 42 is resiliently supported by foam tape 32 which comprises a resilient closed cell polyethylene material while film 42 is cut into islands. In order to cut the islands from foam tape 32 the die cutting edges must quickly severed the film yet not penetrate the foam tape sufficiently far so as to form openings in the foam tape. By having the polyethylene film held in tension as it passes around roller 46 film 42 partially supports itself to permit one to cut islands of polyethylene film while the film is mounted on a resilient foam tape without destroying the gas and liquid impermeability of the foam tape. FIG. 6 illustrates that the closed cell foam tape has an inherent resiliency that permits the die cutting edges to cut through film 42 without cutting through foam tape 32.

I claim:

1. A dynamic non-bandage, wound patch to permit a user with a broken skin wound to engage in physical activities in the proximity of contaminates without contaminating of the wound covered by the wound patch or without having excretions from the wound migrate through the wound patch for a period not to exceed a few hours comprising:

a flexible and resilient layer of material, said flexible and resilient layer of material having sufficient flexibility to dynamically conform to the movement of the skin underlying the wound patch, said flexible and resilient layer of material having an interior region and a peripheral region, said flexible and resilient layer of material comprising a liquid impermeable and gas impermeable material to prevent ingress or egress of gases or liquids through said flexible and resilient layer of material;

a nonabsorbent and non-stick island located in said interior region to permit a user to place said nonabsorbent and non-stick island directly over a bandage on a person; and a layer of liquid and gas impermeable adhesive extending completely across said flexible and resilient layer of material, said layer of liquid and gas impermeable adhesive material coacting with said flexible and resilient layer of material to secure said flexible and resilient layer of material to the skin of a user to temporarily form a liquid and gas impermeable barrier over a wound so that the user can participate in physical activities in the presence of contaminates without contaminating the wound.

2. The dynamic wound patch of claim 1 wherein said wound patch has a rectangular shape with rounded corners.

3. The dynamic wound patch of claim 1 wherein said flexible and resilient layer of material comprises a closed cell polyethylene foam.

4. The dynamic wound patch of claim 1 wherein said non absorbent and non-stick island comprises polyethylene.

5. The dynamic wound patch of claim 1 wherein said wound patch has a rectangular size of approximately 2 inches by 4 inches with the non-stick island being sufficiently large to fit over a bandage on a wound to maintain the bandage in a slidable relationship to the non-stick island.

6. A dynamic wound patch to permit a user to engage in physical activities without contaminating a wound or without having wound excretions migrate through the wound patch for a period of a few hours comprising:

a flexible layer of material having an interior region and a peripheral region, said flexible layer of material comprising a liquid impermeable and vapor impermeable material to prevent ingress or egress of vapors or liquids through sad flexible layer of material having flexibility in excess of the human skin so that said flexible layer of material can dynamically flex and bend in response to the flexing and bending of a users body;

a nonabsorbent and non-stick island located in said interior region to permit a user to place said nonabsorbent and non-stick island directly over a bandage or a wound to permit said non-stick island to move with respect to the underlying bandage or wound; and a layer of flexible adhesive located on said peripheral, said flexible adhesive comprising a liquid and vapor impermeable material, said layer of flexible adhesive operable to secure said flexible layer of material to the skin of a user so that the user can secure the wound patch around bandage to prevent vapors or liquids from contacting the wound through either the adhesive or the flexible layer of material during physical activity of the user.

7. The wound patch of claim 6 wherein the wound patch has an elasticity equal to or greater of the skin of the user.

8. The wound patch of claim 6 wherein said non-stick island is surrounded by an adhesive region that has sufficient tackiness to prevent migration of gas or liquids between the wound patch and the user's skin.

9. The wound patch of claim 6 wherein said adhesive and said gas and liquid impermeable are coextensive with each other.

* * * * *